(12) United States Patent
Caville et al.

(10) Patent No.: US 8,448,283 B2
(45) Date of Patent: May 28, 2013

(54) TOOTHBRUSH WITH DUAL ROTARY BRUSHING SYSTEM

(75) Inventors: Roland Caville, Hong Kong (CN);
Patrick Arnoux, Marseilles (FR);
Jean-Christophe Ferrer, Verrieres le Bruisson (FR)

(73) Assignees: Patrick Arnoux, Marseilles (FR);
Jean-Christophe Ferrer, La Ciotat (FR)

( * ) Notice: Subject to any disclaimer, the term of this patent is extended or adjusted under 35 U.S.C. 154(b) by 293 days.

(21) Appl. No.: 12/812,759

(22) PCT Filed: Jan. 13, 2009

(86) PCT No.: PCT/FR2009/050044
§ 371 (c)(1),
(2), (4) Date: Feb. 14, 2011

(87) PCT Pub. No.: WO2009/092957
PCT Pub. Date: Jul. 30, 2009

(65) Prior Publication Data
US 2011/0138552 A1    Jun. 16, 2011

(30) Foreign Application Priority Data
Jan. 14, 2008   (FR) ...................... 08 00198

(51) Int. Cl.
*A61C 17/26* (2006.01)
(52) U.S. Cl.
USPC .......................................................... 15/23

(58) Field of Classification Search
USPC ............... 15/22.1, 23, 24, 25, 167.1, 230
See application file for complete search history.

(56) References Cited

U.S. PATENT DOCUMENTS

| 2,583,886 | A | * | 1/1952 | Schlegel | 15/23 |
| 2,655,675 | A | * | 10/1953 | Grover | 15/23 |
| 4,313,237 | A | * | 2/1982 | Smith | 15/23 |
| 5,864,911 | A | * | 2/1999 | Arnoux et al. | 15/23 |
| 2008/0052845 | A1 | * | 3/2008 | Djang | 15/23 |

FOREIGN PATENT DOCUMENTS

| DE | 102005007617 | 9/2006 |
| FR | 2293890 | 7/1976 |
| WO | 8700405 | 1/1987 |

* cited by examiner

*Primary Examiner* — Robert Scruggs
(74) *Attorney, Agent, or Firm* — Trego, Hines & Ladenheim, PLLC

(57) ABSTRACT

The invention relates to a mechanical toothbrush with a dual rotary brushing system having a handle and a head fixed on the handle. The head is provided with adjacent contrarotating brushes that are of cylindrical shape and have substantially parallel axes, each of them being supported at least at their distal end by a bearing and each being driven by a shaft. The shafts are flexible and supported by the two bearings to allow the two brushes to move away from and towards each other. The support includes four flexible branches around a central component serving to fix the support on the head composed of a single arm. The support and/or the head of the toothbrush are designed such that the support is fixed on the head while allowing the support to pivot about its point of fixation to the head.

10 Claims, 1 Drawing Sheet

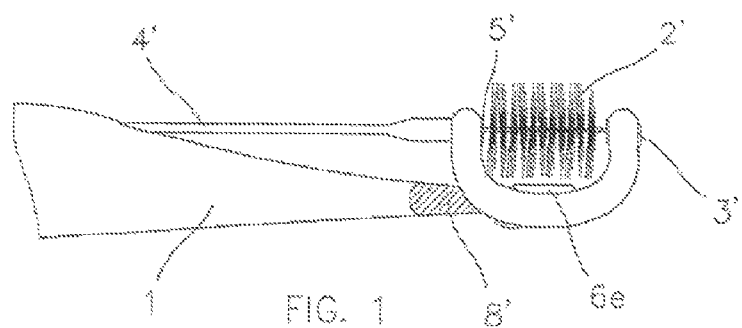
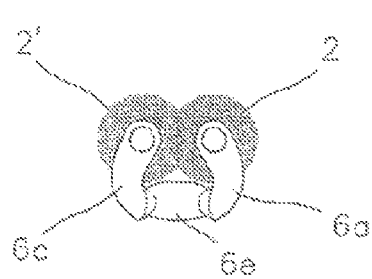
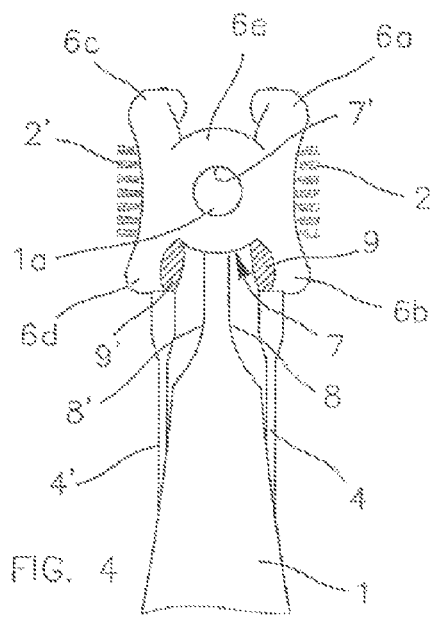
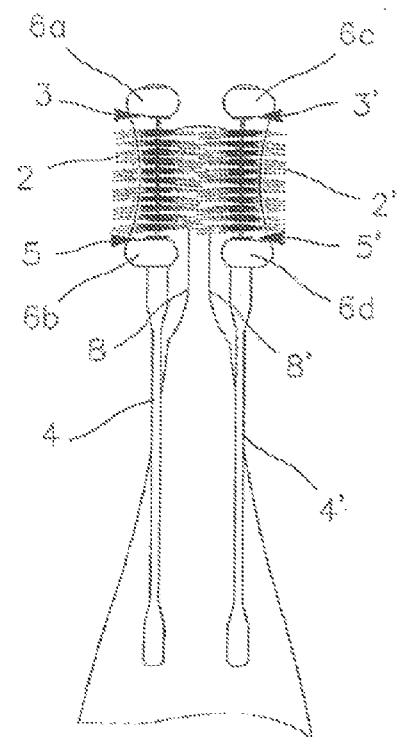
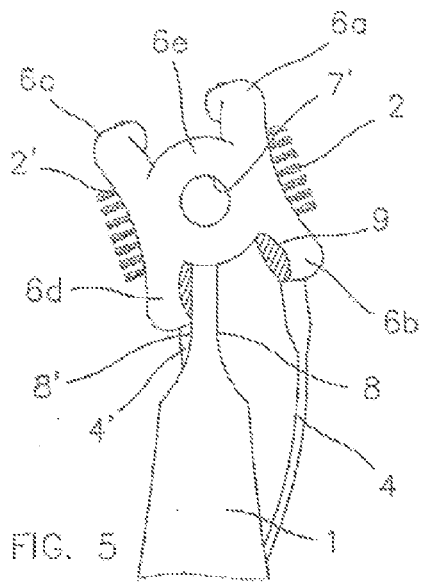

TOOTHBRUSH WITH DUAL ROTARY BRUSHING SYSTEM

This invention has for object a toothbrush having two rotating brushes for the brushing, in particular, a toothbrush with dual rotary brushing system.

It relates to the fields of oral hygiene and of dental care, in particular for humans, but can entirely be adapted to a veterinary use.

Oral hygiene is directly linked to the manner in which the brushing of the teeth is carried out. Indeed, all of the specialists agree that circular brushing is ineffective and that in order to be effective, the brushing of the teeth must be carried out from the gums towards the exterior of the tooth, i.e. from top to bottom pour the upper jawbone and from bottom to top for the lower jawbone.

The selection of a toothbrush is carried out according to several criteria, for example the age, the dental anatomy, the periodontal condition, the hardness of the bristles, etc. A large number of types of different toothbrushes are correctly available on the market. There are manual conventional toothbrushes, electric toothbrushes, with vibrating, alternating or rotating movements. For example, European patent EP 0488971 described an electric toothbrush comprising two contrarotating brushes arranged in order to act on the same blank of the dental arch. It is obvious that in this case, if one of the brushes always works in the proper direction of brushing, the other has to act in the incorrect direction.

None of these devices makes it possible to guarantee a brushing that is always carried out in the best direction, unless an automatic system is integrated inverting the direction of rotation according to the position of the device in the mouth, such a system being complex, expensive and generally with little reliability.

In order to overcome these disadvantages, tooth brushing devices have been developed comprising cylindrical brushes with parallel ones, having rotating movements in the inverse direction and making it possible to insert between then the teeth to be cleaned in such a way that each side of the latter is brushed in the direction of the root towards the end. For example, patent application FR 2 489 120 describes a tooth brushing device of which the cylindrical brushes are separated by a constant distance that is greater than the maximum width of a tooth (about five millimeters) and free at their distal end, i.e. that distanced from the handle wherein is housed the system for driving in rotation said brushes by their other end.

Patent CH 644256 describes a brushing device wherein the brushes are provided with tapered section rods of synthetic material of which the elasticity makes it possible to obtain a certain pressure against the teeth that is clamped between them.

These types of devices necessarily include a means of controlling of the direction of brushing, either via a rotation inserter of the drive motor, or via elbow connectors imposing a determined position of the brushes in relation to the dental arch to be cleaned.

Patent EP 0108097 describes a tooth brushing device having, housed in a well surrounding casing, several interchangeable modules of which one has three cylindrical brushes with parallel axis of large diameters of which the median brush makes possible the brushing of the top of the teeth. However, such a device has the disadvantage of the lack of effectiveness because the median brush has a direction of rotation that is antagonistic to that of one of the lateral brushes and its presence determines a certain height of application of the device which does not always make possible an effective action across the entire height of the teeth and in particular to the gums.

In addition to the disadvantages mentioned hereinabove, most of these known devices have a constant moving away of the brush, which on the one hand requires several heads or several devices to be proposed according to the user (children, adults, etc.) and on the other hand does not make possible for the same user an effectiveness of homogenous brushing for all of the teeth in light of the differences of thickness of teeth (molar teeth, premolar teeth, canine teeth, etc.); and in the devices of the type described in patent CH 644256 which are the only devices to allow for a moving away of the brushes due to the fact of the mounting of the latter on flexible shafts but held at their single base, other than the disadvantage of the control of direction of brushing mentioned previously, they do not allow for a homogenous pressing on the teeth since their moving away cannot adapt to the width of the teeth across their entire length and such an arrangement induces in any case shearing and bending forces on the drive shafts which are then damaged over time.

In order to attempt to overcome these difficulties, patent application FR 2662598 has been taken and the brushing device described in this patent application is of the type of that described in application FR 2489120. It comprises two contrarotating brushes with rigid axes, free at their distal ends and maintained by the opposite ones providing for their driving. They are contained in a casing which comprises a guide wherein one of the ends of the brushes can be displaced by separation from the other according to an arc of circle ensuring the continuity of its driving around and via a gear drive, and thanks to a cable and spring device. The purpose of this device is then to adapt to any thickness of tooth and to maintain a constant pressure on the latter and in a quasi-homogenous manner across the entire length of the brushes which must for this remain quasi-parallel during the brushing. However, such a device lacks in reliability, facility of use, particularly during the positioning in the mouth due to its size and consequently it does encourage the use of it.

Patent EP 0 725 602 described a toothbrush of this type i.e. a mechanical toothbrush with dual rotary brushing system comprising a body forming a handle and a head fixed on said handle, head notch being provided with two adjacent contrarotating brushes that are of a cylindrical shape and have substantially parallel axes, each supported at least at their distal end by a bearing and each driven by a flexible shaft located in the head and supported at least by a bearing, the shafts carrying said brushes being flexible and each one of said two bearings which support them, one located at their end and the other on the side of the body being mounted on a support allowing the two brushes to move away from each other and then ensuring that they move towards each other via recall effect. These supports thus allow for the brushes to move away from each other and also ensure that they move towards each other by spring effect due to the elasticity of the support common to the two brushes. These supports are mounted in a casing that is more or less open extending the head of the device and which surrounds at least partially the brushes.

Although such toothbrushes have many advantages since they make it possible in particular to ensure a brushing always taking place in the ideal direction, and to simultaneously carry out the cleaning of the two sides of the dental arch, which results in a certain redaction in the brushing time, they nevertheless have certain disadvantages, in particular linked to the form of the supports of brushes and of the casing which surrounds at least partially the brushes or even because of the arms which carry the brushes.

Indeed, it has been observed that the presence of this casing or of these arms generates an encumbrance in the mouth which can be uncomfortable for the user.

In order to overcome such a disadvantage, the inventors have proposed a toothbrush of the type described hereinabove wherein the spatial encumbrance of the brush has been reduced while still preserving all of these qualities. Indeed, this mechanical toothbrush with dual rotary brushing system proposes to suppress the casing by replacing it advantageously with a support allowing the two brushes to move away from each other and then ensuring that they move towards each other. Said support comprises four flexible branches, around a central component used for the fastening of said support on the head constituted of a single arm. In this central component, there is either an orifice which can be snapped onto a protruding lug carried by the head, or, more preferably, two orifices: an orifice forming a handle allowing for the passage of the head and another orifice allowing for the snapping of the head in this central portion thanks to the engagement, in said orifice of the central portion, of a lug arranged protruding on said single arm.

As such, advantageously, the central component makes it possible to easily fix said support on the head in the form of a single arm in such a way that the toothbrush constituted as such has a reduced encumbrance and therefore aliens for a more pleasant use.

However, although this device clearly improves the capacity of brushing of the teeth due to its reduced dimension and its maneuverability with regards to toothbrushes of prior art exposed hereinabove, it nevertheless has the disadvantage of its lack of adaptability and of its limited flexibility in the mouth and on the teeth of the user. These disadvantages harm the optimal brushing of the teeth.

As such, this invention has for purpose to overcome such a disadvantage by proposing a toothbrush of this type having flexibility, an increased maneuverability thanks to a greater degree of freedom of pivoting of the brushes with regards to the teeth.

To this effect, this invention has for object a mechanical toothbrush with dual rotary brushing system comprising a body forming a handle and a head fixed on said handle, head which is provided with adjacent contrarotating brushes that are of a cylindrical shape and have substantially parallel axes, each supported at least at their distal end by a bearing and each driven by a shaft on the head, said shapes being flexible and each one of the said two bearings that support them, one located at their distal end and the other on the side of the body, being mounted on a support, allowing the two brushes to move away from each other and then ensuring that they move towards each other, the support comprising four flexible branches, around a central component used for the fastening of said support on the head constituted of a single arm, characterized in that the support and/or the head of the toothbrush are arranged so that the support is fixed on the head while still authorizing a pivoting of the support around its fastening on the head.

A better maneuverability of the toothbrush is as such offered during the brushing and therefore a more effective brushing. Indeed, the authorized pivoting of the support in relation to the longitudinal axis of the head allows for better maneuverability in the mouth.

According to the preferred embodiment of the invention, a mechanical toothbrush is therefore proposed with dual rotary brushing system comprising a body forming a handle and a head fixed on said handle, which head provided with adjacent contrarotating brushes that are of a cylindrical shape and have substantially parallel axes, each supported at least at their distal end by a bearing and each driven by a shaft on the head, said shafts being flexible and each one of said two bearings that support them, one located at their distal end and the other on the side of the body, being mounted on a support, allowing the two brushes to move away from each other and then ensuring that they move towards each other, the support comprising four flexible branches, around a central component used for the fastening of said support on the head constituted of a single arm, the central component comprising two orifices, the first orifice used for the passage of the distal portion of the head and the second orifice used for the snapping of the central component on a lug arranged protruding on the single arm constituting the head of the toothbrush, characterized in that a play is arranged between the distal portion of the head and the first orifice wherein it is engaged.

As such, once the fastening is finalized by the lug of the head snapping into the second orifice of the support, the play that exists between the orifice forming a handle of engagement of the head and the head at its distal end towards the central component authorizes a pivoting of the support in relation to the head around said lug.

As such, this play can be obtained by a support having an orifice that is wider than the head that crosses through it, and/or by the head which has a more tapered shape at its distal end. Furthermore, the head can include two recesses, respectively one on each lateral side of the head in its distal portion, below the lug allowing for its fastening and on its portion engaged in the orifice of the support forming a handle.

This offers an amplitude of pivoting of the support with regards to the head which supports it, which allows for a greater degree of freedom of pivoting of the two brushes and therefore improved maneuverability and as such a better effectiveness of brushing of the teeth.

Also, according to one or the other or both of the characteristics of this embodiment, the support can as such actually pivot amply around the lug carried by the head.

This is possible particularly by the fact that a portion of two flexible branches oriented towards the handle of the toothbrush are recessed in their respective internal portion, this allowing even further the pivoting of the support around the fastening lug by offering a greater degree of freedom of pivoting of the support with regards to the head carrying it.

In a particularly advantageous manner, when the toothbrush according to this invention has the combination of branches of the support having recesses and of the head also having recesses, a particular substantial pivoting can be obtained because a wide space is released between the head and the branches of the support as such offering a greater freedom of movement. The two branches oriented towards the handle of the toothbrush will be able to be housed in the recesses arranged an said distal portion of the head. During the maximum pivoting of the support with regards to the head, this internal portion of the branches oriented towards the handle of the toothbrush will come into contact and bear against said respective recesses of each lateral side of the head. The more the end of the head is thin, tapered, streamlined, the higher the freedom of pivoting of the support carrying the brushes around the lug carried by the head. These recesses will make possible a movement and a range of positioning of the brushes that is much wider than those offered not only by the toothbrushes of prior art but also by a toothbrush according to the invention comprising only the recesses on the central portion and the two branches oriented towards the handle.

As such, advantageously, the central component makes it possible to easily fix said support on the head in the form of a single arm in such a way that the toothbrush constituted as such has a reduced encumbrance and therefore allows for a more pleasant use but especially increased maneuverability. The brushing of the teeth will be further effective as the brushes will be able to be oriented according to the relief encountered in the mouth of the user and adapt their direction without being hindered by the encumbrance of the head which carries them.

The pairs of branches of the support are arranged on each side of the central fastening component, said pairs of branches substantially having the shape of a U of which the proximal ends, located close to the body, and distal, located on the other side of the body each show a bearing surrounding a rotating brush and each one of said two proximal bearings each supporting a flexible shaft.

As such, the support according to this invention has substantially an X shape when viewed from above, with the brushes oriented towards the floor.

More preferably, said support is carried out in the form of a single part in a flexible material such as a thermoplastic elastomer, in particular a thermoplastic elastomer without plasticizer, such polyether block amide known under the trade name Pebax.

The invention shall now be described in more detail in reference to the drawing wherein:

FIG. 1 shows a lateral perspective view of a toothbrush head according to an example embodiment of the invention;

FIG. 2 shows a perspective view of the top of the head in FIG. 1;

FIG. 3 shows a front perspective view of the head in FIG. 1; and

FIG. 4 shoes a rear perspective view of the head in FIG. 1.

FIG. 5 shows a top view of the head in FIG. 1 when the support is in its position of maximum pivoting.

The device or brush according to this invention comprises a hollow body serving as a handle (not shown) wherein the means of power supply (transformer for an exterior power and/or electric accumulator and/or battery) as well as the drive motor of the brushes 2, 2' are housed.

The device further comprises a head 1 which can be disconnected, uncoupled from the hollow body in order to be interchangeable. This head 1 is provided at its end with two adjacent rotating brushes 2, 2' of cylindrical shape and that have substantially parallel axes.

The system for driving the brushes 2, 2' is similar to that described in EP 0 725 602 and shall not be included here in further detail.

Each brush 2, 2' as supported at least at its distal end by a bearing 3, 3' and each driven by a shaft 4, 4' on the head 1, said shafts 4, 4' being flexible. Each one of said two bearings which support the shafts 4, 4', one 3, 3' located at their distal end, corresponding to the bearing of the brush also, and the other proximal 5, 5' of the side of the body, is mounted on a support 6 allowing the two brushes 2, 2' to move away from each other and then ensuring that they move towards each other.

This support 6 comprises four flexible branches 6a, 6b, 6c and 6d positioned around a central component 6a used for the fastening of said support 6 on the head 1.

Advantageously, the central component 6e makes it possible to fix said support 6 on the head 1 and this thanks to the presence on said central component 6e of two orifices 7 and 7'. The first orifice 7 forming a handle is used for the introduction of the head 1 into the central component 6e. The second orifice 7' of the central component 6e allows for the clipping or snapping on the lug 1a arranged protruding on the single arm constituting the head of the toothbrush and whereon the central component 6e is engaged. The orifices 7 and 7' are located more preferably in two perpendicular planes in relation to one another.

In such a way as to generate the play authorizing the pivoting between the support 6 and the head 1, this support 6 comprises a cavity on each side of the orifice 7 which further enlarges this orifice 7 in relation to the head engaged therein as well as on each of the internal portions of the branches 6b and 6d in order to form a recess 9, 9' making possible a more ample pivoting of said support 6 with regards to the head 1. These recesses 9, 9' are designed to generate and increase the freedom and the amplitude of the movement of the support 6 in relation to the head 1. This is shown in FIG. 5.

This head 1 has more preferably the form of a single arm with a tapered shape at its distal end and furthermore has more preferably recesses 8, 8' on each side of the distal tapered portion located between the branches 6a and 6d of the support 6 and engaged in the orifice 7. These recesses 8, 8' make it possible to further increase the possibility of movement of the support 6 in relation to the head 1. The pivoting of the brushes can as such be more ample as there will be less stress and a less-frequent thrust bearing between the branches and the head 1 in this zone located between the branches 6b and 6d. This is shown in FIG. 5. In the case of a maximum pivoting of the support 6 in relation to the head 1, as illustrated in FIG. 5, the branch 6d partially covers the tapered portion of the head 1, the latter being due to the fact that this portion of the head 1 is housed in the recess 9' of the branch 6d.

In this FIG. 5, it is also possible to see that when the support 6 is in its position of maximum pivoting, the arms 4, 4' bend in order to adapt as best as possible to the movement.

This head 1 also has at its distal end a lug 1a arranged protruding from said arm perpendicularly to the longitudinal axis of the head. This lug 1a is provided to be housed in the orifice 7' of the central component 6e, the pivoting of the support 6 being carried out around said lug 1a.

One pair of branches 6a, 6b and 6c, 6d of the support 6 is arranged on each side of the central fastening component 6e. Each pair of branches 6a, 6b; 6c, 6d has substantially the shape of a U, each one of said two bearings which support the flexible shafts 4, 4', one 3, 3' located at their distal end and the other 5, 5' on the side of the body being mounted at the ends of the U.

The base of each U is integral with the central component 6e in such a way that the U extends in a plane substantially perpendicular to the central component 6e. As such, the support 6 has substantially an X shape of which the ends are flexible allowing the two brushes 2, 2' fixed thereon to move away from each other and to move towards each other.

More preferably, each branch of a U can furthermore be arranged curved towards the interior of the head 1, in order to accentuate the effect of the brushes 2, 2' moving towards each other in idle position of the brush while still allowing them to move away from each other due to the flexibility of each branch but with an elastic recall effect which as such maintains during the brushing a pressure of the brushes 2, 2' on the teeth. This elastic recall can be advantageously obtained thanks to the material in which the support 6 is carried out.

The invention claimed is:

1. A mechanical toothbrush with dual rotary brushing system comprising a body forming a handle and a head fixed on said handle, said head provided with adjacent contrarotating brushes that are of a cylindrical shape and have substantially parallel axes, each supported at least at their distal end by a bearing and each driven by a shaft on the head, said shafts being flexible and each one of said two bearings which support them, one located at their distal end and the other on the side of the body, being mounted on a support, allowing the two brushes to move away from each other and then ensuring that they move towards each other, the support comprising four flexible branches around a central component used for the fastening of said support on the head constituted of a single arm, characterized in that the support and/or the head of the toothbrush are arranged so that the support is fixed on the head while still authorizing a pivoting of said support around its fastening on the head.

2. A mechanical toothbrush with dual rotary brushing system comprising a body forming a handle and a head fixed on said handle, head which is provided with adjacent contrarotating brushes that are of a cylindrical shape and have substantially parallel axes, each supported at least at their distal end by a bearing and each driven by a shaft on the head, said shafts being flexible and each one of said two bearings which support them, one located at their distal end and the other on the side of the body, being mounted on a support, allowing the two brushes to move away from each other and then ensuring that they move towards each other, the support comprising four flexible branches around a central component used for the fastening of said support on the head constituted of a single arm, the central component comprising two orifices, the first orifice forming a handle used for the passage of the distal portion of the head and the second orifice used for the snapping of the central component on a lug arranged protruding on the single arm constituting the head of the toothbrush, characterized in that a play is arranged between the distal portion of the head orifice wherein it is engaged.

3. Toothbrush according to claim 2, characterized in that the first orifice forming a handle of the central component is wider than the distal portion of the head passing through it and/or the head is tapered at its distal end, towards the central component.

4. Toothbrush according to claim 3, characterized in that the head, at its distal end, comprises two recesses, respectively one of each lateral body of the head in its distal portion.

5. Toothbrush according to claim 2, characterized in that the flexible branches of the support oriented towards the handle of the toothbrush respectively have a recess in their internal portion allowing for the pivoting of the support around the lug.

6. Toothbrush according to claim 2, characterized in that a pair of branches of the support is arranged on each side of the fastening component.

7. Toothbrush according to claim 6, characterized in that each pair of branches substantially have the form of a U, each one of said two bearings which support the flexible shafts, one located at their distal end and the other on the side of the body being mounted at the ends of the U.

8. Toothbrush according to claim 7, characterized in that a base of each U is integral with the central component in such a way that the U extends in a plane substantially perpendicular to the central component, the support substantially having an X shape of which the ends are flexible allowing the two brushes fixed thereon to move away from each other and to move towards each other.

9. Toothbrush according to claim 7, characterized in that each branch of a U is arranged curved towards the interior of the head.

10. Toothbrush according to claim 2, characterized in that said support is carried out in the form of a single part in a flexible thermoplastic elastomer without plasticizer.

\* \* \* \* \*